US00PP08981P

United States Patent [19]

Glicenstein

[11] Patent Number: Plant 8,981

[45] Date of Patent: Nov. 15, 1994

[54] CHRYSANTHEMUM PLANT NAMED AUTUMN DENISE

[75] Inventor: Leon Glicenstein, Salinas, Calif.

[73] Assignee: Yoder Brothers, Inc., Barberton, Ohio

[21] Appl. No.: 143,155

[22] Filed: Oct. 29, 1993

[51] Int. Cl.[5] ..... A01H 5/00

[52] U.S. Cl. ..... Plt./79

[58] Field of Search ..... Plt. 76, 79, 74.1, 82.3

[56] References Cited

U.S. PATENT DOCUMENTS 4,616,099 10/1986 Sparkes ..... 47/58

OTHER PUBLICATIONS

Broertjes, et al., 1980, "A mutant of a mutant of a . . . Irradiation of progressive radiation-induced mutants in a mutation breeding programme with *Chrysanthemum morifolium*", Euphytica, 29:526–530.

Gosling, ed., 1979, "The Chrysanthemum Manual–6th edition", The National Chrysanthemum Society, London, Essex Telegraph Press, Ltd., pp. 329–336.

Broertjes, et al., 1978, "Application of Mutation Breeding Methods In the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Yoder Brothers, Inc. 1993. "1994–95 Garden Mums". 19 pages.

*Primary Examiner*—Howard J. Locker

*Attorney, Agent, or Firm*—Foley & Lardner

[57] ABSTRACT

A Chrysanthemum plant named Autumn Denise particularly characterized by its flat capitulum form; spooned decorative capitulum type; light red-bronze ray floret color; diameter across face of capitulum of 76 to 89 mm when fully opened; branching pattern is spreading and prolific, with 6 to 9 breaks after pinch when grown outside under natural daylength in fall flowerings, and 6 to 7 breaks after pinch when grown in 10 cm pots for spring flowerings; natural season flower date of August 25 to September 3 when planting rooted cuttings on June 21 to June 23 in Salinas, Calif., and September 30 when planting rooted cuttings June 11 in Hightstown, N.J.; flowering response of 45 to 49 days after rooting in no light/no shade programs in spring; plant height of 33 cm when grown in fall under natural daylength with no growth regulators in New Jersey, 25 to 30 cm when grown in 10 cm pots in spring with no applications of 2500 ppm B-9 SP; and durable, uniform performance.

1 Drawing Sheet

The present invention comprises a new and distinct cultivar of Chrysanthemum, botanically known as *Dendranthema grandiflora*, and referred to by the cultivar name Autumn Denise.

Autumn Denise, identified as 8019 (88-308E01), is a product of a mutation induction program. The new cultivar was discovered and selected by Leon Glicenstein on Jul. 8, 1991, in a controlled environment in Salinas, Calif. as one flowering plant within a flowering block established as rooted cuttings from stock plants which had been exposed as unrooted cuttings to an X-ray source of 2000 rads in Fort Myers, Fla. on Mar. 6, 1991. The irradiated parent cultivar was the cultivar identified as Denise, disclosed in U.S. Plant Pat. No. 8,178, and described as a garden mum with a flat spooned decorative flower; greyed-orange ray floret color; diameter across face of capitulum of 76 to 89 mm when fully opened; spreading and prolific branching pattern, with 6 to 9 breaks after pinch when grown outside under natural daylength in fall flowerings, and 5 to 8 breaks after pinch when grown in 10 cm pots for spring flowerings; natural season flowering date of August 25 to 31 when planting rooted cuttings June 21 to 23 in Salinas, Calif., and September 30 to October 15 when planting rooted cuttings June 11 to June 18 in Highstown, N.J.; flowering response of 45 to 49 days after rooting in no light/no shade programs in spring; plant height of 30 to 41 cm when grown in fall under natural daylength with no growth regulators in New Jersey, 25 to 30 cm when grown in fall under natural daylength with no growth regulators in California, and 21 to 25 cm when grown in 10 cm pots in spring with 0 to 2 applications of 2500 ppm B-9 SP. The ranges of measurements for Denise given here are wider than the measurements given in the plant patent for Denise. This is based on continuing flowering trials of Denise after filing the plant patent application for Denise.

The irradiation program resulting in Autumn Denise had as its primary objective the expansion of color ranges of the parent cultivar Denise. The irradiation program comprised irradiating cuttings of the parent cultivar at irradiation levels of 1500, 1750 and 2000 rads. A total of 1299 cuttings harvested from a total of 225 irradiated plants were planted on May 13 and 6, 1991, respectively. Of these, 26 initial selections were made, which selections were then revegetated and reflowered. Three consecutive flowerings resulted in discarding 20 of the original 26 selections on Mar. 19, 1992. Two codes were reselected, which reselections were ultimately discarded on Nov. 10, 1992. The remaining six selections were maintained as PIs (Possible Introductions) and further trialed in Salinas, Calif., Hightstown, N.J. and Leamington, Ontario, Canada, ultimately resulting in the decision to discard four of these codes on Oct. 1, 1992 and to introduce selection 8019 as Autumn Denise and selection 8032 as Sunny Denise. Sunny Denise is disclosed in pending plant patent application Ser. No. 08/168,174.

The first act of asexual reproduction of Autumn Denise was accomplished when vegetative cuttings were taken from the initial selection in September 1991 in a controlled environment in Salinas, Calif., by technicians working under supervision of Leon Glicenstein.

Horticultural examination of controlled flowerings of successive plantings has shown that the unique combination of characteristics as herein disclosed for Autumn Denise are firmly fixed and are retained through successive generations of asexual reproduction.

Autumn Denise has not been observed under all possible environmental conditions. The phenotype may vary significantly with variations in environment such as temperature, light intensity and daylength, without, however, any variation in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial greenhouse practice for small pot spring garden mum production.

The following traits have been repeatedly observed and are determined to be basic characteristics of Autumn Denise, which, in combination, distinguish this Chrysanthemum as a new and distinct cultivar:

1. Flat capitulum form.
2. Spooned decorative capitulum type.
3. Light red-bronze ray floret color.
4. Diameter across face of capitulum of 76 to 89 mm when fully opened.
5. Branching pattern is spreading and prolific, with 6 to 9 breaks after pinch when grown outside under natural daylength in fall flowerings, and 6 to 7 breaks after pinch when grown in 10 cm pots for spring flowerings.
6. Natural season flower date of August 25 to September 3 when planting rooted cuttings on June 21 to June 23 in Salinas, Calif., and September 30 when planting rooted cuttings June 11 in Highstown, N.J.
7. Flowering response of 45 to 49 days after rooting in no light/no shade programs in spring.
8. Plant height of 33 cm when grown in fall under natural daylength with no growth regulators in New Jersey, 25 to 30 cm when grown in fall under natural daylength in California, and 21 cm when grown in 10 cm pots in spring with no applications of 2500 ppm B-9 SP.
9. Durable, uniform performance.

The accompanying photographic drawing is a color photographic of Autumn Denise grown as a pinched garden mum under natural season outside conditions in Salinas, Calif., with the colors being as nearly true as possible with illustrations of this type. Plants were grown outside and dug and transplanted into 15 cm bulb pans at flowering time for photography purposes.

Of the commercial cultivars known to the inventor, the most similar in the comparison to Autumn Denise is the parent cultivar Denise. In the above description of Autumn Denise, the ranges of values for Autumn Denise are much narrower than the ranges of values given for Denise. This is based on the fact that Denise was flowered over many years, while Autumn Denise was flowered over a period of only one and a half years. All traits of Autumn Denise are similar to those of Denise, except for the ray floret color. The ray floret color of Autumn Denise is light red-bronze, much darker than the greyed-orange ray floret color of Denise. This color difference is particularly pronounced in spring greenhouse pot programs. In fall, outdoor natural season flowerings, Denise develops more pigments under the higher light intensity prevalent under outdoor conditions as compared to greenhouse conditions. However, even in the fall, Autumn Denise is significantly darker than Denise.

In the following description color references are made to The Royal Horticultural Society Colour Chart. The color values were determined on plant material grown as a pinched garden mum grown under natural season outside conditions in Salinas, Calif. on Aug. 27, 1993.

Classification:

*Botanical.*—*Dendranthema grandiflora* cv Autumn Denise.

*Commercial.*—Flat spooned decorative spray pot mum and garden mum.

INFLORESCENCE

A. Capitulum:

*Form.*—Flat.

*Type.*—Spooned decorative.

*Diameter across face.*—76 to 89 mm when fully opened.

B. Corolla of ray florets:

*Color (general tonality from a distance of three meters).*—Light red-bronze.

*Color (upper surface).*—Fully mature petal tips closest to 173C. Immature petals 173C, tinged with 179B.

*Color (under surface).*—163D, tinged with 179B.

*Shape.*—Spooned, with large section of the ray floret flattened and spoon-like, giving the impression of a decorative capitulum type.

C. Corolla of disc florets:

*Color (mature).*—14B.

*Color (immature).*—144B.

D. Reproductive organs:

*Androecium.*—Present on disc florets only, no to very scant pollen.

*Gynoecium.*—Present on both ray and disc florets.

PLANT

A. General Appearance:

*Height.*—33 cm when grown in fall under natural daylength with no growth regulators in New Jersey, 25 to 30 cm when grown in fall under natural daylength in California, and 21 cm when grown in 10 cm pots in spring with no applications of 2500 ppm B-9 SP.

*Branching pattern.*—Spreading and prolific, with 6 to 9 breaks after pinch when grown outside under natural daylength in fall flowerings, and 6 to 7 breaks after pinch when grown in 10 cm pots for spring flowerings.

B. Foliage:

*Color (upper surface).*—147A.

*Color (under surface).*—147B.

I claim:

1. A new and distinct Chrysanthemum plant named Autumn Denise, as described and illustrated.

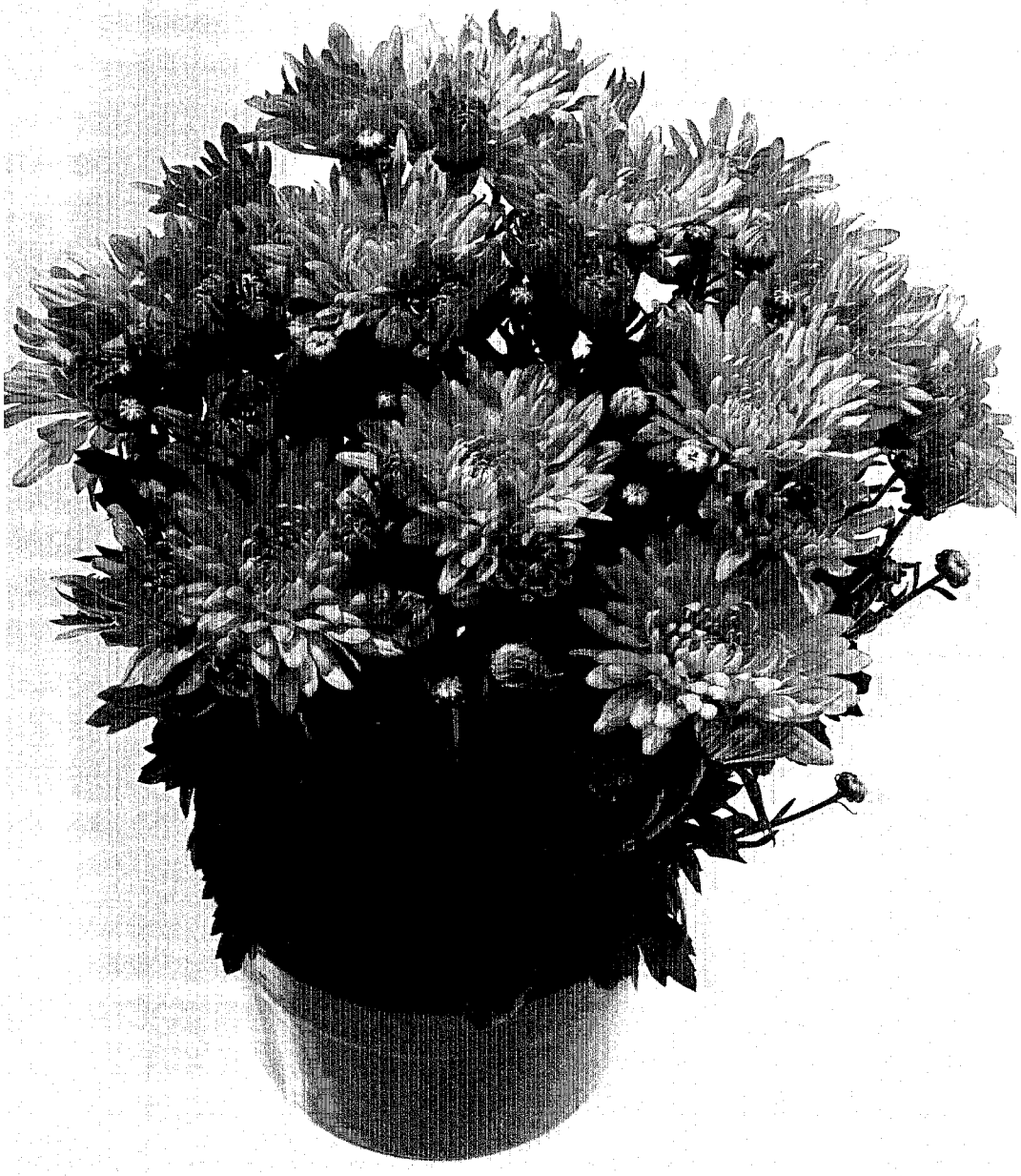

* * * * *